(12) United States Patent
Silverman et al.

(10) Patent No.: US 8,521,453 B1
(45) Date of Patent: Aug. 27, 2013

(54) WIRELESS SENSOR AND DATA MANAGEMENT SYSTEM AND METHOD FOR MONITORING THE INTEGRITY OF MECHANICAL STRUCTURES

(75) Inventors: Eugene B. Silverman, Great Cacapon, WV (US); Nischom K. Silverman, Albuquerque, NM (US); Paul Baity, Great Cacapon, WV (US)

(73) Assignee: Berkeley Springs Instruments LLC, Cumberland, MD (US)

( * ) Notice: Subject to any disclaimer, the term of this patent is extended or adjusted under 35 U.S.C. 154(b) by 266 days.

(21) Appl. No.: 12/724,186

(22) Filed: Mar. 15, 2010

(51) Int. Cl.
*G01F 17/00* (2006.01)
*H04B 15/00* (2006.01)

(52) U.S. Cl.
USPC .............. 702/56; 702/171; 702/183; 702/189

(58) Field of Classification Search
USPC .............. 702/56–63, 121–123, 171, 183–190
See application file for complete search history.

(56) References Cited

U.S. PATENT DOCUMENTS

2007/0085606 A1* 4/2007 Thomas et al. ............... 330/254

* cited by examiner

*Primary Examiner* — Phuong Huynh
(74) *Attorney, Agent, or Firm* — Birch, Stewart, Kolasch & Birch, LLP (57) ABSTRACT

A method and apparatus for inspecting a wall of a mechanical structure including obtaining an infinite response from a sample material having a front face, a thickness, and a back wall, by transmitting into a sample material an ultrasonic wave having a frequency and duration and being generated by one or more transducers, wherein the thickness of the sample material is sufficiently great that only a wave corresponding to the front face of the sample is received back; transmitting an ultrasonic wave generated by one or more transducers into the wall of a mechanical structure to be inspected at a time (T), wherein the ultrasonic wave has the same frequency and duration as the ultrasonic wave transmitted into the sample material; receiving a response signal back from the wall to be inspected; and correlating the response signal to the infinite response, thereby creating correlated data. The system can be operated remotely and wirelessly, and data can be transmitted and received via the Internet or local area network, either wireless or wired.

20 Claims, 14 Drawing Sheets

WE USE A .5 INCH IMMERSION TRANSDUCER WITH 3.5 MHz RESONANT FREQUENCY.

EACH IMAGE THAT IS SHOWN IS ACCOMPANIED BY A DATA FILE. THE FORMAT OF THE DATE FILE IS A SAMPLE NUMBER FOLLOWED BY THE VALUE. FOLLOWING ARE SOME TYPICAL VALUES:
29,-0.2025817
30,-0.20969
31,-0.207614
32,-0.2091013
33,-0.2015194

THIS IS THE WAVE THAT IS TRANSMITTED TO THE TRANSDUCER: (FILE NAME: 1_6_35e40MHz.flt)

THIS CHIRP GOES FROM 1 TO 6 MHz AND IS 35 uSECS LONG. IT IS PRODUCED WITH 40 MHz DAC. THE IDEA OF IT WAS TO HAVE SMALL AMPLITUDE AT 3.5 MHz, THE RESONANT FREQUENCY OF THE TRANSDUCER.

WE HAVE ALSO USED CHIRPS WITH THE FOLLOWING SHAPE:   FIG. 9

WIRELESS SENSOR AND DATA MANAGEMENT SYSTEM AND METHOD FOR MONITORING THE INTEGRITY OF MECHANICAL STRUCTURES

FIELD OF INVENTION

The invention relates to electrical communications, and more specifically to acoustic wave systems and devices.

BACKGROUND

Monitoring the mechanical integrity of pipelines, offshore production platforms, storage tanks and associated equipment is a complex problem. This is due to a wide variety of operational issues, especially those associated with the remote location of these structures. Current practice requires the dispatching of personnel to remote locations in order to conduct inspections of these assets using a variety of non-destructive inspection techniques. One particular area of integrity monitoring and measurement relates to the corrosion or loss of metal of these before-mentioned structures.

Measurement techniques commonly found in the industry include eddy current instruments, guided wave ultrasound, phased array ultrasound and direct ultrasound thickness measurements, to name a few. The use of ultrasound can be conveniently categorized as an ultrasound testing (UT) method. See Krautkramer, Josef and Krautkramer, Herbert, Ultrasonic Testing of Materials, 4th/revised edition, Springer Verlag, November 1990. In the case of pipeline corrosion monitoring there are typically three measurement techniques: (1) In-Line Inspection (ILI), (2) intrusive and (2) non-intrusive techniques.

In-Line Inspection (ILI) tools, or smart pigs, are intelligent sensing devices that are introduced into the line at a specialized entry point and most commonly conveyed by product flow along the length of the pipe. Although there are significant advantages to pipeline pigging, there are a number of operational complexities and limitations. In addition, this process is expensive and invasive to a pipelines operation. See Pipeline Pigging Handbook by Jim Cordell and Hershel Vanzant, CLARION Technical Publishers; 3RD edition, 2003.

Intrusive methods include electrical resistance probes and coupons. The coupon is the original form of intrusive corrosion monitoring. It can typically consist of a strip of metal made of material similar to the pipeline. It is weighed, then inserted it into an access point and left for several months for exposure to the product. The operator then removes the coupon and weighs it again to see what percentage is missing. As in any invasive technique, this approach to corrosion monitoring can be disruptive to pipeline operations. See Lawson, K. M., and N. G. Thompson. "The Use of Coupons for Monitoring the Cathodic Protection of Buried Structures.," CORROSION/98, paper no. 672. Houston, Tex.: NACE, 1998.

The most common non-intrusive device is external monitoring such as eddy current testing and ultrasonic testing (UT) as cited earlier. In either case, in order to conduct a survey, a defined area is excavated around the pipeline and a portable device (pulser-receiver) is held against the pipe. Within the UT sensor, voltage is applied across a piezoelectric crystal to generate an ultrasonic sound wave that propagates through the metal. The time it takes to travel through the metal and back to the transducer is directly proportional to its thickness. The devices are quick, easy to use and inexpensive, and operators do not have to shut off flow or risk breeching the pipeline in order to take a reading. On the other hand, there are significant costs for digging up the pipeline each time a test is conducted. These labor costs are also high when the pipeline owner must dispatch inspectors to evaluate fixed locations on above ground pipelines, pipeline transitions and pipeline components. This is also the case for offshore pipeline structural components that are monitored on a routine basis both above and below the structure's waterline.

There are a number of other corrosion monitoring techniques available to the industry. Most, if not all, remote monitoring techniques use indirect measurement methods such as electrochemical potentials. See McMurry, John; Robert C. Fay (March 2004). "Electrochemistry", Chemistry, 3rd Edition, Prentice Hall.

The problem with most measurement techniques is that:

1. The before mentioned measurement techniques require personnel to travel to asset location in order to take the measurement. Wireless networks exist for remote monitoring of flow, pressure, fugitive emissions and similar applications; however, most non-destructive measurements typically require the intervention of personnel in order to acquire the measurements;

2. Measurement tools typically require a power source that must be either available locally or accompanied with the person taking the measurement;

3. The location of many of these before-mentioned assets is difficult to access which poses safety risks to the inspectors;

4. Most permanent installations of remote measurement sensors are invasive and require some degree of operational downtime;

5. The environment in which measurements are taken can be potentially explosive; therefore, not all measurement techniques are possible without special intrinsically-safe equipment; and, 6. Mechanical degradation rates of some assets can be rapid, requiring frequent integrity assessment measurements, further increasing the personnel safety risk and operational cost.

SUMMARY OF INVENTION

The present invention solves before-mentioned problems by providing an ultrasonic sensor system with minimal power requirements which enables the system to be operated and monitored wirelessly and remotely.

A first aspect of the invention is a method for inspecting a wall of a mechanical structure, including obtaining an infinite response from a sample material having a front face, a thickness, and a back wall, by transmitting into a sample material an ultrasonic wave having a frequency and duration and being generated by one or more transducers, wherein the thickness of the sample material is sufficiently great that only a wave corresponding to the front face of the sample is received back; transmitting an ultrasonic wave generated by one or more transducers into the wall of a mechanical structure to be inspected at a time (T), wherein the ultrasonic wave has the same frequency and duration as the ultrasonic wave transmitted into the sample material; receiving a response signal back from the wall to be inspected; and correlating the response signal to the infinite response, thereby creating correlated data.

A second aspect of the invention is a mechanical structure monitoring system, including one or more transducers for transmitting a broadband long pulse ultrasonic wave into a mechanical structure to be monitored and for receiving a response signal back from the mechanical structure, wherein the mechanical structure has a front face, a thickness, and a back wall; a central processing unit for eliminating noise from the response signal wave form; a means for transmitting the response signal waveform to a remotely-located server and for receiving data back from the remotely-located server; and a user terminal for accessing the transmitting means thereby allowing a user to pulse or energize the transducer in order to transmit the broadband long pulse ultrasonic wave into the mechanical structure to be monitored.

A feature of the invention is that it can use traditional high resolution ultrasound compression waves although the application can be applied to alternative non-destructive techniques such as shear waves, phased arrays, guided wave ultrasound, eddy current and electromagnetic acoustic transducers.

Another feature of the invention is that single or multiple transducers can be pulsed in any order of interest to the user and, as an alternative feature, would provide for a configuration of a multitude of sensors that can be arranged in an array.

Another feature of the invention is that an array of transducers can be arranged in the shape of a circle, oval, square or rectangular matrix or along one or more axes for a length or shape determined by the monitoring area of interest.

An advantage of the invention is that the system employs low power ultrasonic electronics, thereby making the system intrinsically safe (IS). "Intrinsically safe" equipment is defined as "equipment and wiring which is incapable of releasing sufficient electrical or thermal energy under normal or abnormal conditions to cause ignition of a specific hazardous atmospheric mixture in its most easily ignited concentration."

Another advantage of the invention is that sensors can be located in remote locations with or without a local source of power, and sensors can be located in air or submerged in a liquid such as an aboveground or belowground storage tank, or under water such as an off-shore platform.

A feature of the invention is that it provides thickness measurements with resolution capabilities equal to traditional ultrasound compression waves or similar to phased array or guided wave ultrasound. The sensors can provide measurements on structures with or without coatings, and the sensors can be attached to a structure with the use of glues, clamps, weldments or other forms of permanent or removable attachment methods.

Another feature of the invention is that it provides for the ability to integrate a wide range of sensors that would benefit the user when located in remote monitoring locations. These sensors may include seismic monitoring, monitoring of volatile organic compounds in the atmosphere or local environment, moisture, temperature, nitrogen oxides, carbon dioxide, carbon monoxide, accelerometers used to measure natural or man-made vibrations, and similar sensors used for the remote monitoring of naturally occurring or manmade events.

An advantage of the invention is that it can be monitored remotely via a wireless network accessible through the World Wide Web or in an alternative configuration accessible within a local wireless network, cellular network or local area network. The system allows the user who is logged onto the system to remotely pulse or energize the transducer.

Another advantage of the invention is that it can be packaged for use in non-explosive atmospheres and in locations requiring electronics designed for operation in explosive atmospheres.

Another advantage of the invention is that real time monitoring and control capability is possible from a remote location, either above or below ground; data can be integrated directly into mechanical integrity database management programs for real time or offline analysis; data trending with failure prediction information is readily accessible to the user; and, the system provides early failure warning based on a material loss threshold or, in an alternative configuration, thresholds of special interest to the user.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 20 is an example of a graphic user interface for a system of monitoring thickness of a mechanical structure over time.

DETAILED DESCRIPTION

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention.

Figure 1:
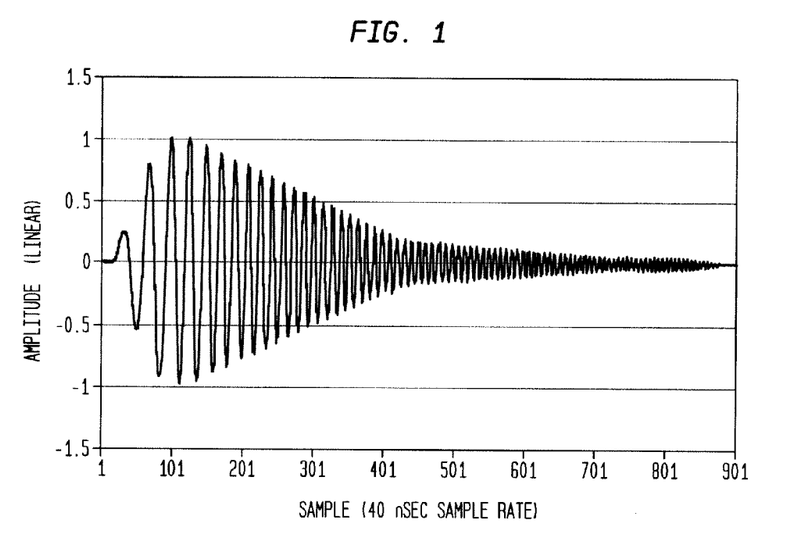
FIG. 1 is a graph plotting an example of a typical long pulse broadband ultrasound wave, or "chirp," transmitted to inspect a wall of a mechanical structure.

Referring generally to FIG. 1, there is shown an exemplary broadband long pulse ultrasound wave or signal which can be used to inspect a wall of a mechanical structure. "Mechanical structure" as used in this application can mean any structure that contains a wall or surface the integrity or thickness of which needs to be monitored from time to time. Non-limiting examples of mechanical structures can include tank or tankers, ships, plates of steel, pipes, bridges or trusses of bridges, wind turbines, off-shore oil platfoims, and pylons. An ultrasonic wave such as that shown in FIG. 1 can be transmitted for between about 10 μseconds to about 50 μseconds, with a preferred duration of about 30 μseconds to about 35 μseconds when the transducer is within about ½" of the wall of the mechanical structure to be inspected. This wave also can be called a "transmit signal." The duration of the transmit signal can be proportional to the distance from the transducer to the wall of the mechanical structure to be inspected. For example, the closer the transducer to the wall, the shorter the preferred duration of the transmit signal; and conversely, the further the transducer from the wall, the longer the preferred duration of the transmit signal. The duration of the transmit signal shown in FIG. 1 was about 35 μseconds. Also, as shown in FIG. 1 the preferred transmit signal is a chirp. A "chirp" signal is a signal in which the frequency increases ("up-chirp") or decreases ("down-chirp") with time. As used herein, the term "chirp" can be used interchangeably with "sweep signal."

Figure 2:
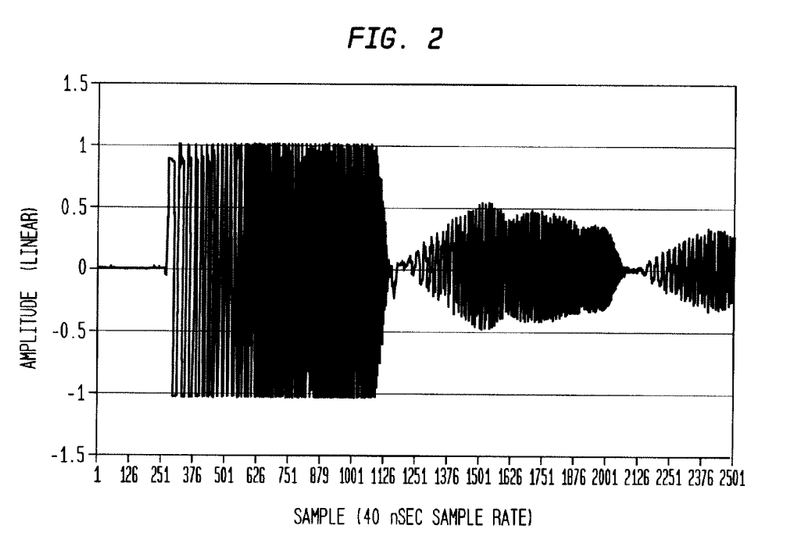
FIG. 2 is a graph showing received calibration data.
Figure 3:
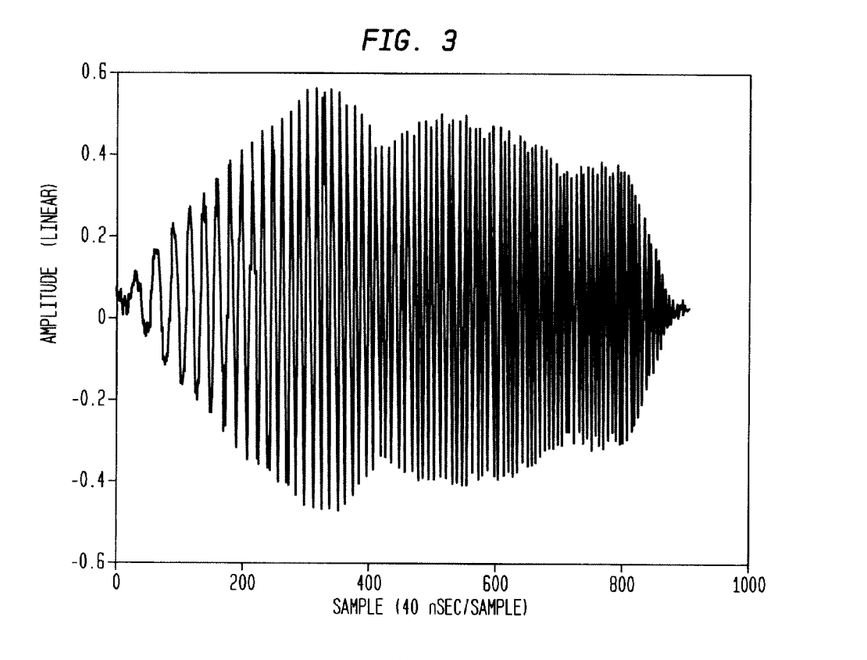
FIG. 3 is an enlarged view of the graph in FIG. 2 showing the desired section of the calibration signal, which is also known as the infinite response.

As shown in FIG. 2, an infinite response (also known as a "calibration signal") can be generated by transmitting a chirp signal into a thick piece of metal sample material. The back wall deflection of the chirp signal is delayed until the 2126 sample shown in the graph. The saturated area in the graph is the transmit time, and the middle signal is the correlation signal which can be used for correlating a response signal to the infinite response. The delay between the correlation data and the back wall deflection allows the correlation data to be isolated for later use. In a preferred embodiment, the sample material is sufficiently thick that a wave corresponding to the back wall of the sample material is not received back, which is why the calibration signal is also known as an "infinite response." For purposes of this application, "calibration signal" and "infinite response" are synonymous and may be used interchangeably. FIG. 3 shows the desired part of the calibration signal which can be used for correlation with a response signal from a mechanical structure to be inspected. There preferably will be a calibration signal for each transducer and transmit signal used.

Figure 4:
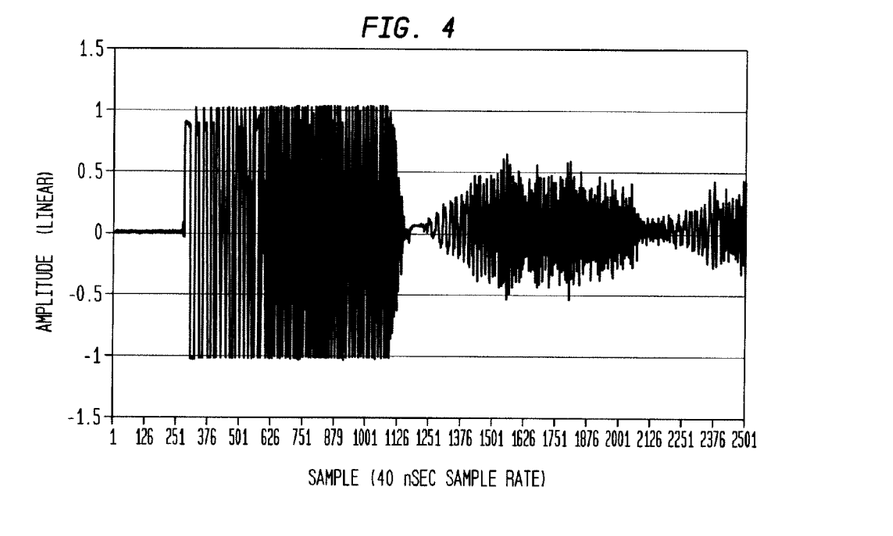
FIG. 4 is a graph showing an ultrasound signal received back from a 0.201 inch thick piece of metal.
Figure 5:
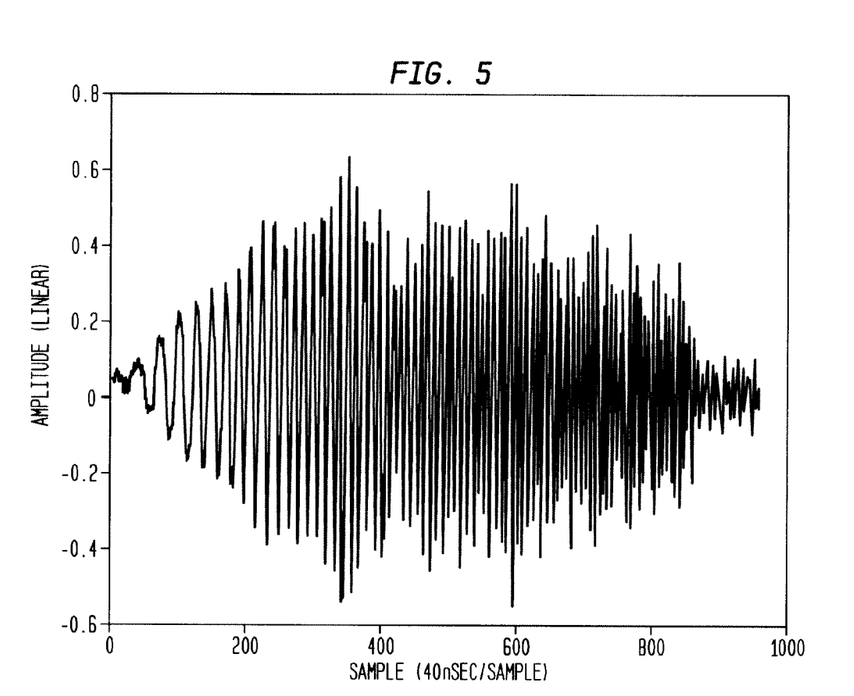
FIG. 5 is an enlarged view of the graph in FIG. 4 showing the desired section of the calibration signal.

FIG. 4 shows another example of a calibration signal received back from a piece of metal having a thickness of about 0.201 inch. As shown in FIG. 3, the saturated area is the transmit time and the second signal is the desired calibration signal. FIG. 5 shows the calibration signal received from the metal sample material of FIG. 4. The portion of the received signal shown in FIG. 5 can be captured by the ultrasound AD/DA board, and normally would be integer data with a −8192 to +8191 range for a 14 bit AD converter. The data can be packaged in a binary file in a row and column format.

Figure 6:
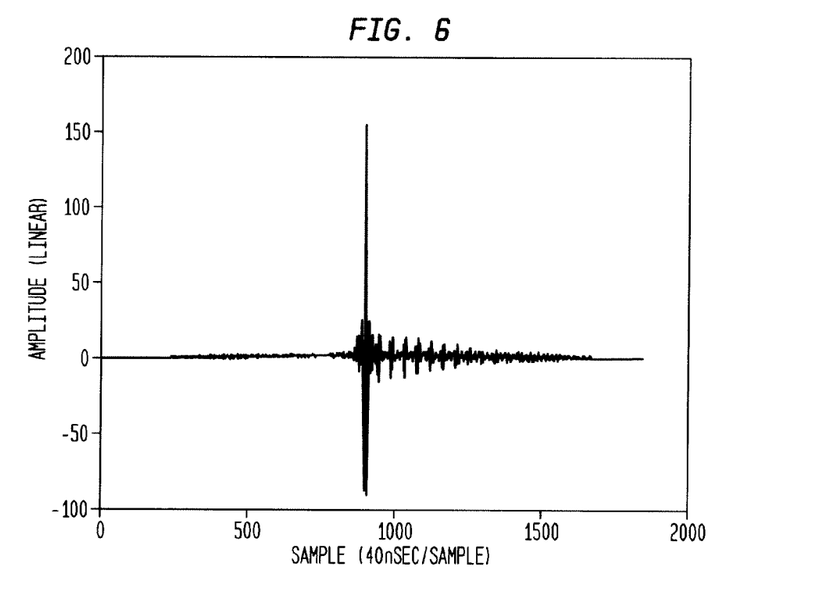
FIG. 6 is a graph showing the received signal from FIG. 5 after the noise is eliminated, thereby creating correlation (or "correlated") data.

Referring generally to FIG. 6, when a calibration signal is correlated with a response signal received back from a mechanical structure to be inspected, correlation data as shown in the graph in FIG. 6 is created. The graph shows a typical A-Scan plot with the big impulse being the reflection back from the front face and the remaining pulses are reflections from the front and back faces. The time between peaks represents the thickness of the metal as represented by the formula:

$$t\text{peak--peak (μsec)}*\text{velocity (inches/μsec)}/2=\text{thickness (inches)}$$

Figure 7:
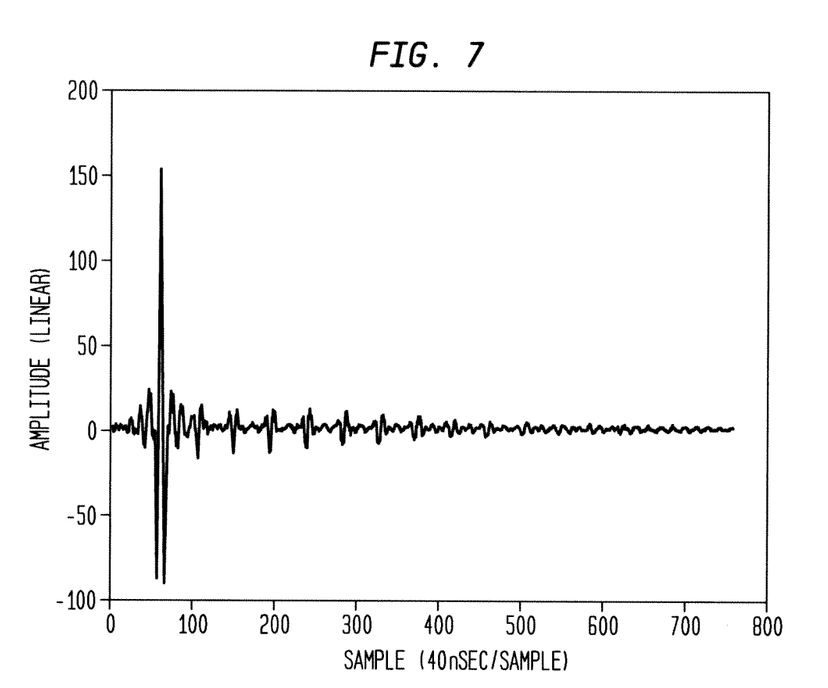
FIG. 7 is an enlarged view of the correlation data from FIG. 6.

An enlarged view of the correlation data from FIG. 6 is shown in FIG. 7. An operator can place cursors on the adjacent peaks to measure time or thickness.

Figure 8:
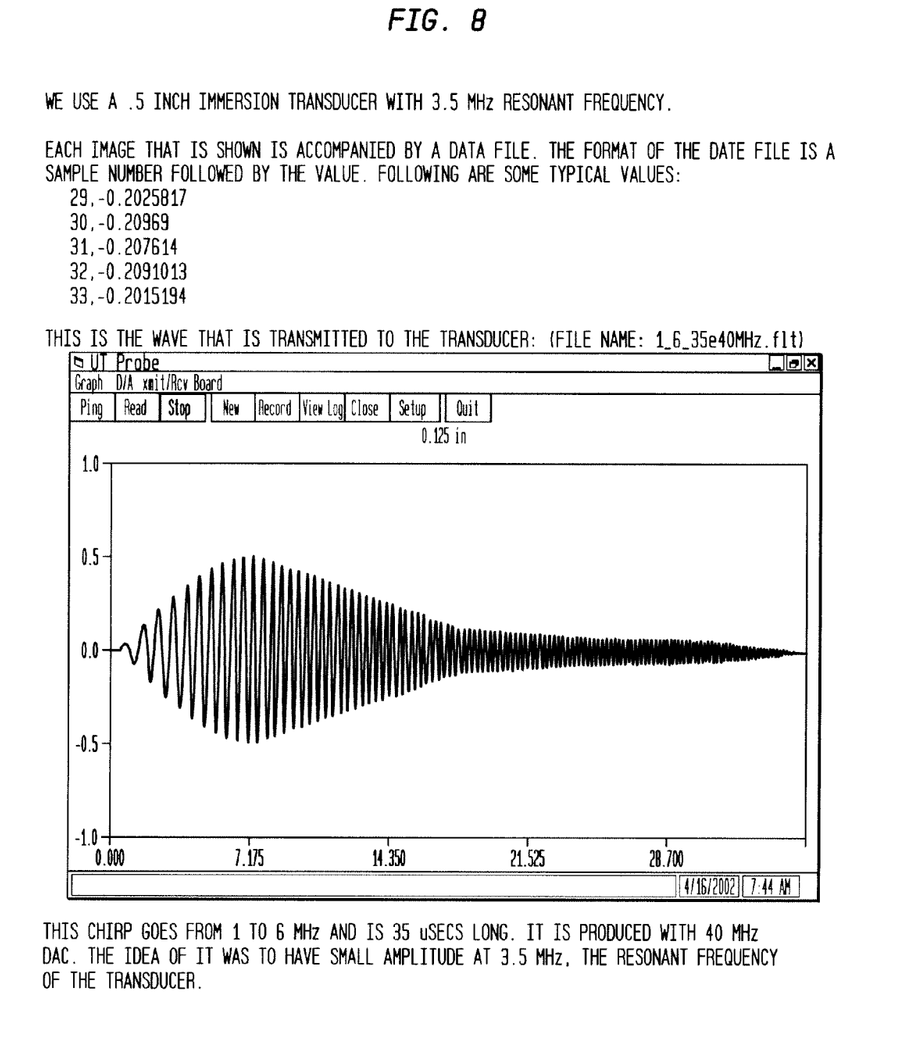
FIG. 8 is a graph plotting an example of a long pulse broadband ultrasound wave, (or "chirp"), transmitted to inspect a wall of a mechanical structure.
Figure 9:
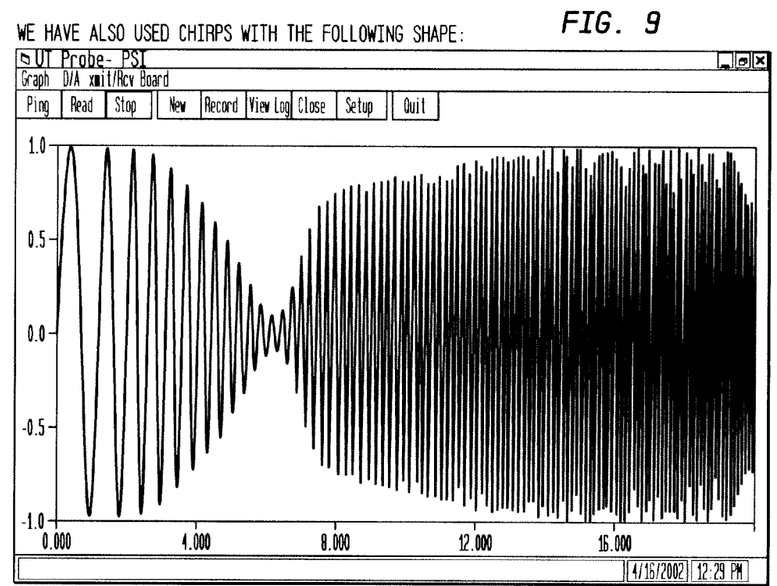
FIG. 9 is a graph of another example of a long pulse broadband ultrasound wave, (or "chirp"), transmitted to inspect a wall of a mechanical structure.

FIGS. 8 and 9 show alternative broadband long pulse ultrasound waves that can be used in the present invention. As with the signal in FIG. 1, these ultrasound signals are chirp signals in which the frequency changes over time.

Figure 10:
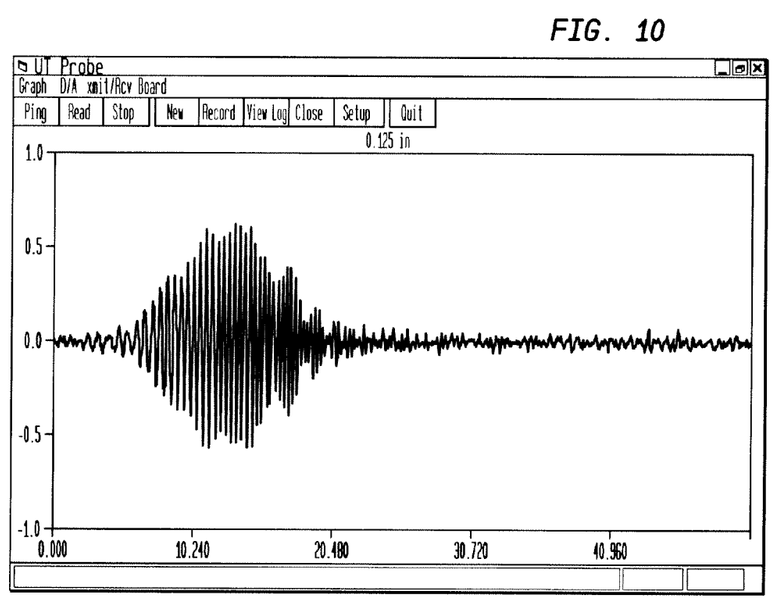
FIG. 10 is a graph showing a return signal.
Figure 11:
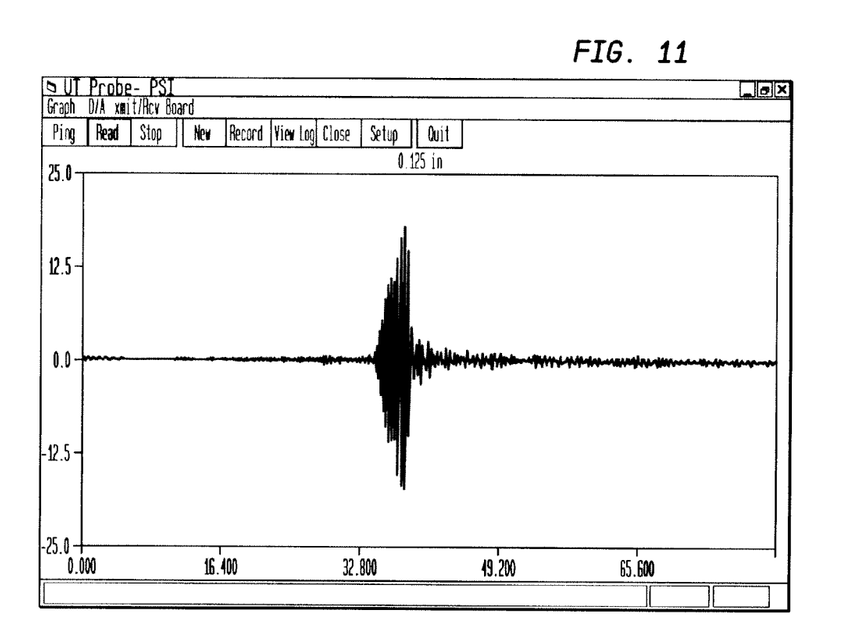
FIG. 11 is a graph showing a calibration wave (or "infinite response")
Figure 12:
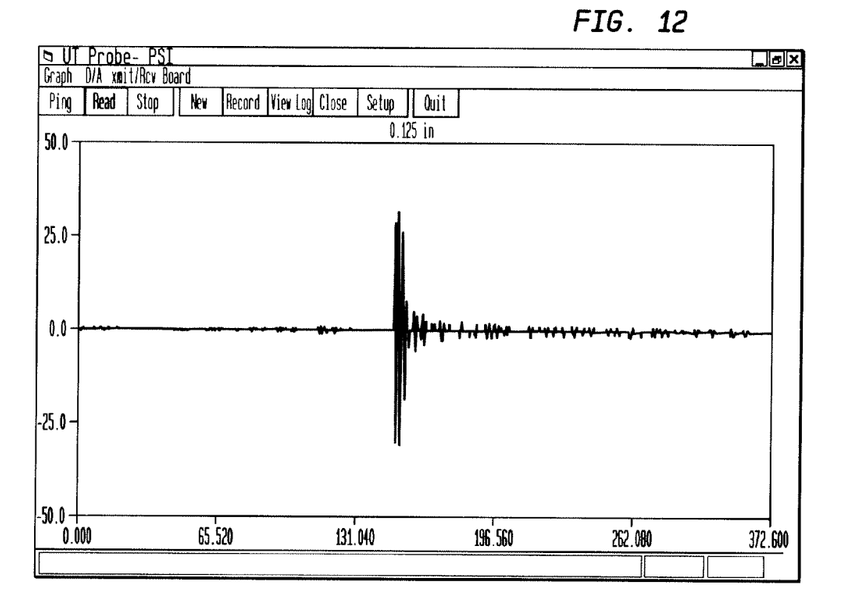
FIG. 12 is a graph correlating the return signal from FIG. 10 with the infinite response from FIG. 11.

FIG. 10 shows a response signal received back from a wall of a mechanical structure to be tested. As shown in FIG. 12, the response signal can be correlated with a calibration signal resulting in correlated data, which is reflected in the graph in FIG. 11. The calibration signal was obtained by recording the infinite response from a thick (approximately 4 inches) block of steel sample material. There is no contribution in the correlated data from internal reflections—only the reflection from the front face—because of the thickness of the sample material. The peaks in the correlated data in FIG. 12 can be analyzed to determine the thickness of the mechanical structure to be inspected.

Figure 13:
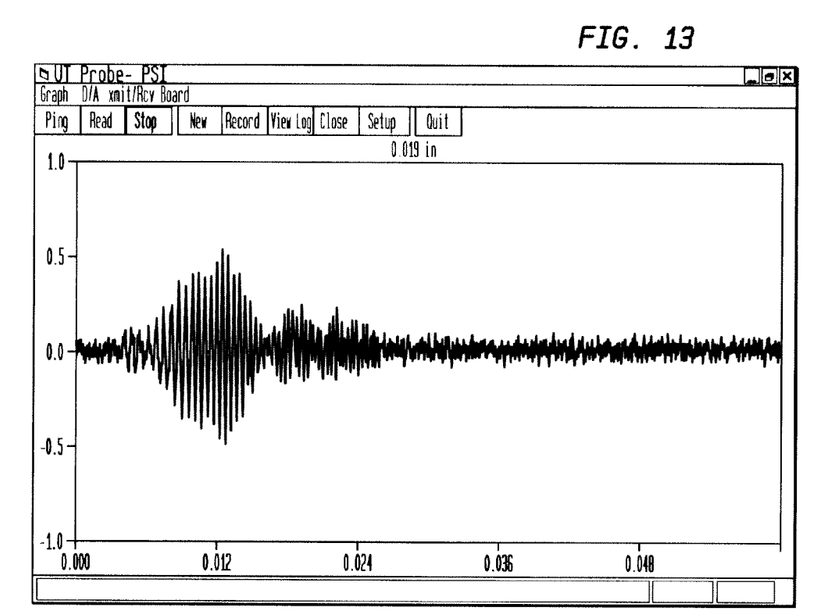
FIG. 13 is a graph plotting a response signal from a corroded plate.
Figure 14:
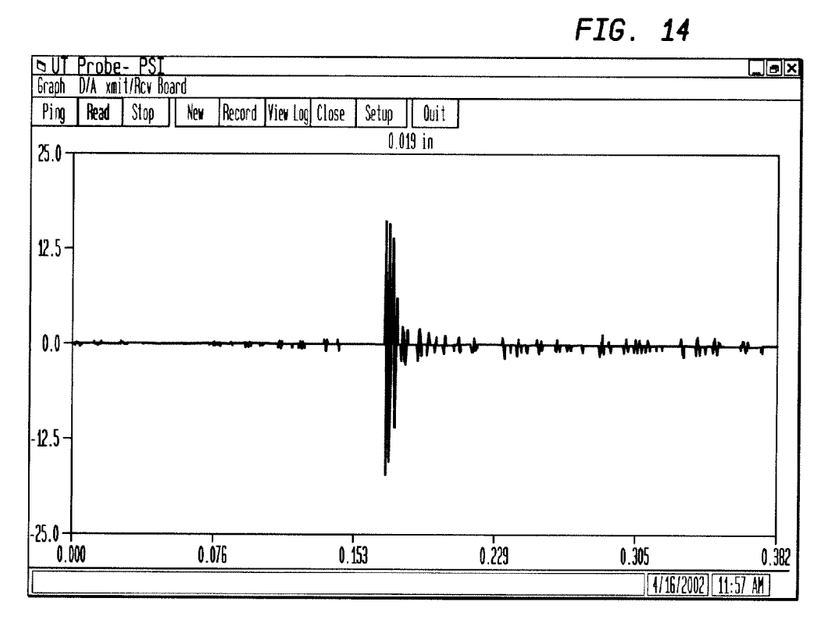
FIG. 14 is a graph showing the response signal from FIG. 13 after correlation with an infinite response.
Figure 15:
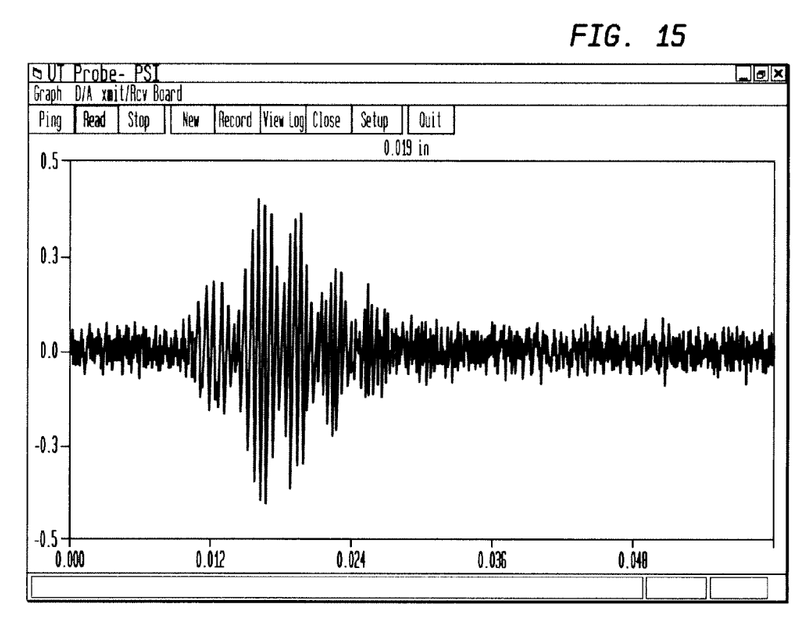
FIG. 15 is a graph showing a response signal when the one or more transducers are tilted when delivering a chirp to a mechanical structure.
Figure 16:
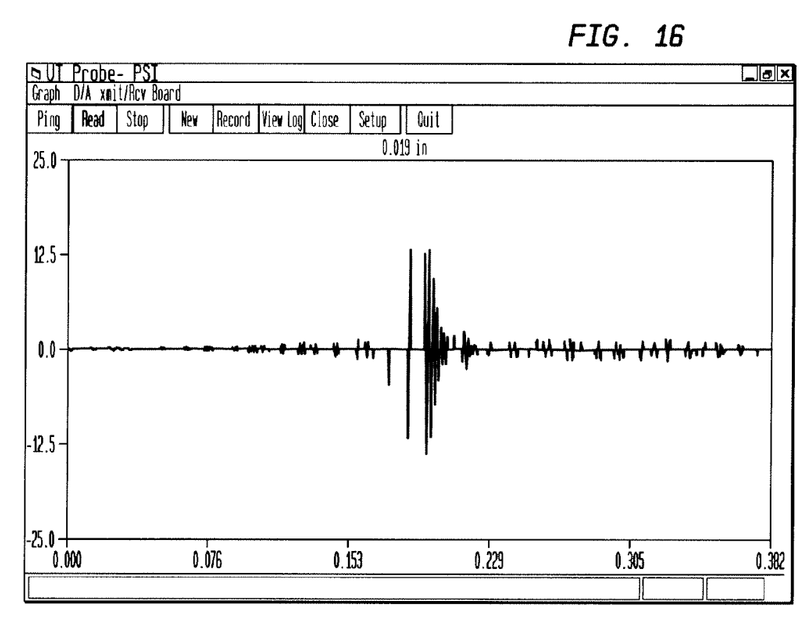
FIG. 16 is a graph showing the response signal from FIG. 15 after correlation with an infinite response.

FIGS. 13 and 14 show a response signal received back from a plate in a mechanical structure to be inspected and correlated data, respectively. Much of the noise has been removed from the correlated data, which reveal corrosion and/or pitting in the plate.

Figure 17:
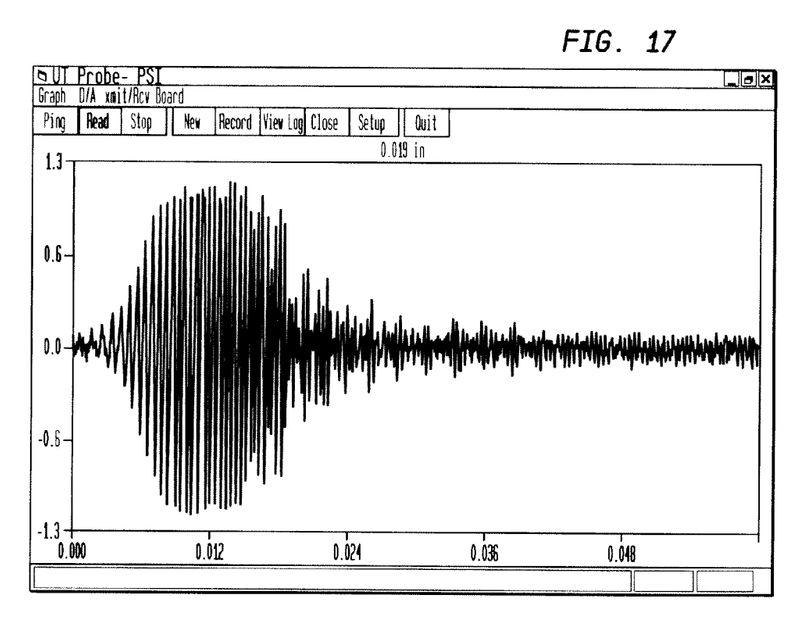
FIG. 17 is a graph showing a response signal from a tank having sludge with water on top.
Figure 18:
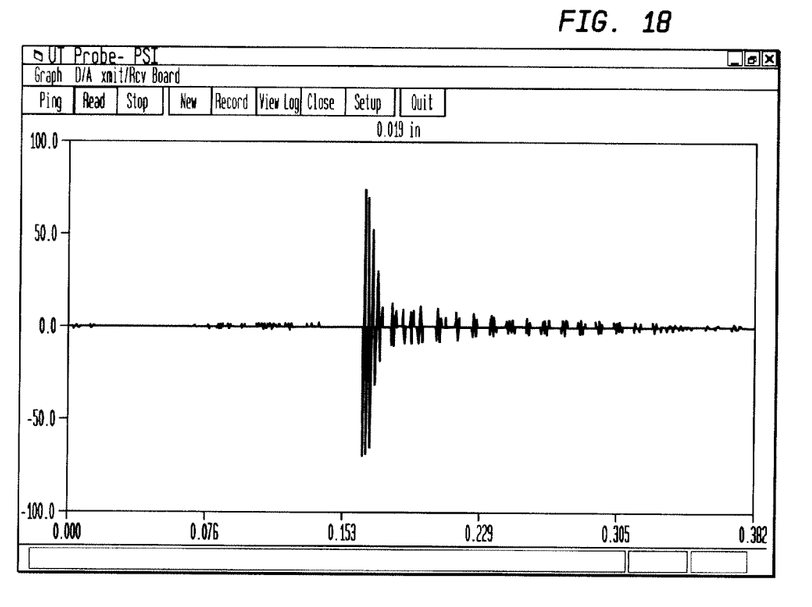
FIG. 18 is a graph showing the response signal from FIG. 17 after correlation with an infinite response.

FIGS. 15 through 18 show response signals and correlation data for mechanical structures where (i) the transducer was tilted and the plate was corroded (FIGS. 15 and 16) and (ii) there was sludge between the transducer and the tank floor (FIGS. 17 and 18).

Figure 19:
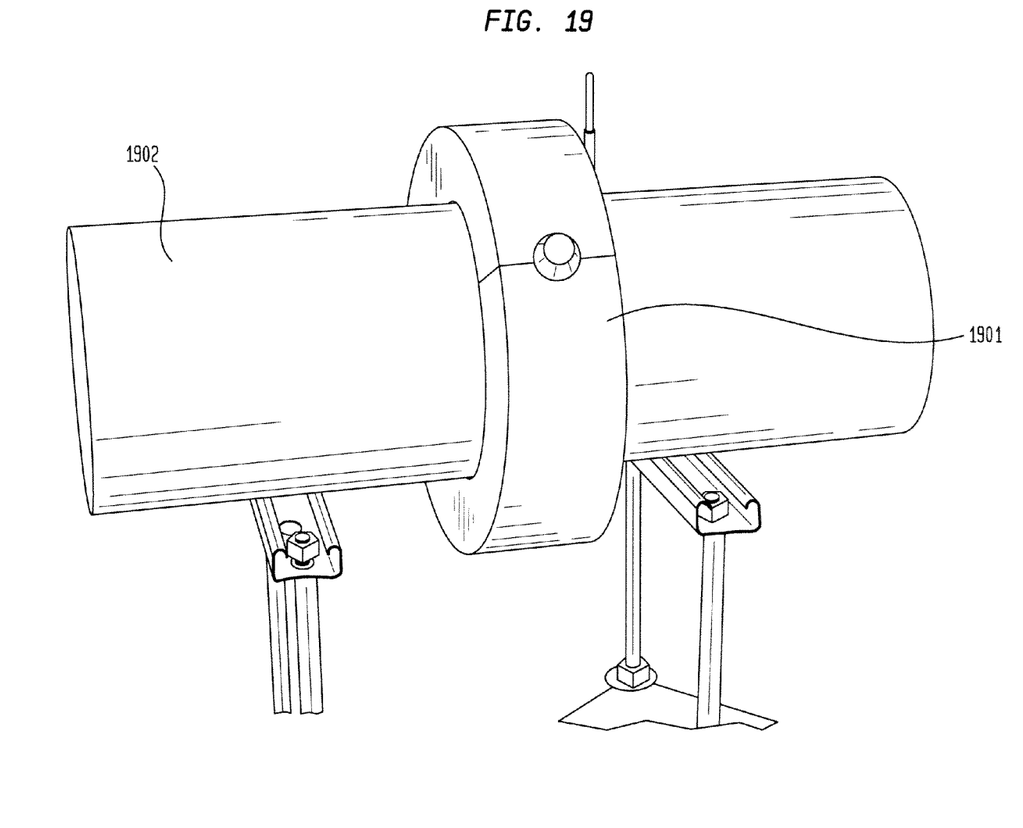
FIG. 19 is a front perspective drawing of an embodiment of a transducer array mounted on a test pipe.

FIG. 19 shows an example of one possible embodiment of a sensor 1901 containing a transducer array mounted on a 6-inch diameter pipe 1901. The sensor 1901 also can include sensor for monitoring humidity, temperature, moisture, structural vibration, wind, atmospheric volatile organic compounds, or seismic activity.

Figure 21:
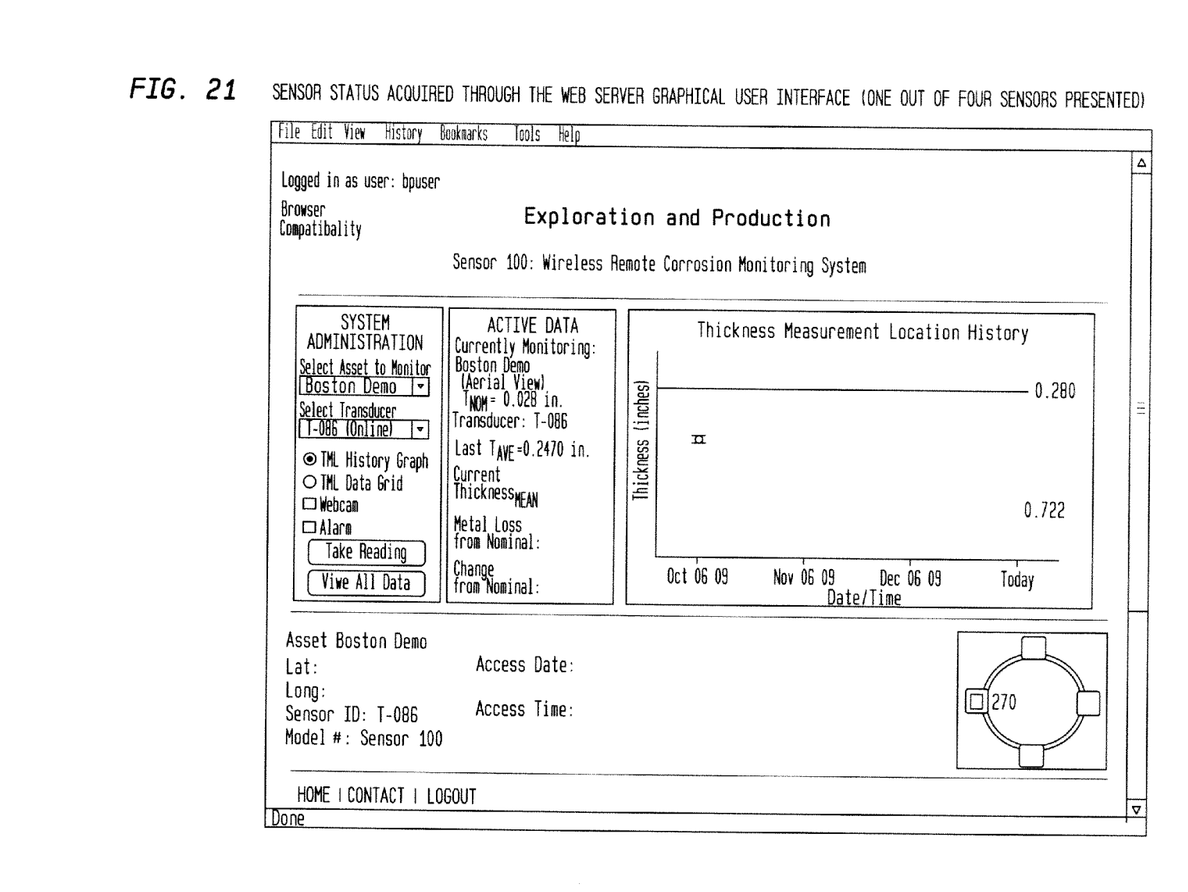
FIG. 21 is a schematic showing a mechanical structure monitoring system network.

As shown most clearly in FIG. 21, the method and system of the present invention can be implemented and monitored remotely. The system can include one or more transducers for transmitting a broadband long pulse ultrasonic wave into a mechanical structure to be monitored and for receiving a response signal back from the mechanical structure, wherein the mechanical structure has a front face, a thickness, and a back wall. The system can also include additional environmental sensors, such as sensors for monitoring humidity, temperature, moisture, structural vibration, wind, atmospheric volatile organic compounds, or seismic activity. A central process unit can be included either onsite in the sensor array or at a remote site for eliminate noise from a response signal received back from a mechanical structure to be inspected. A means for transmitting the response signal to a remotely located server and for receiving data back from the remote serve can be included. Non-limiting examples of transmitting means include a wired or wireless connection to the Internet or other local area network with secure encrypted data transmission. Unlike prior ultrasound systems used for nondestructive testing which cannot be operated remotely due, at least in part, to their power requirements, the system of the present invention requires not more than about 12 volts of electrical force and can operate with as little as 5 volts of electrical force. This low power requirement allows the invention to be wirelessly operated remotely. As a result, the system can be powered by the sun or a battery for extended periods of time. The system can further include auxiliary power means and/or a battery backup for powering the one or more transducers and environmental sensors. The system can be an Internet-accessible system that allows the user to pulse a remotely located ultrasonic sensor that is permanently attached to a corroded pipe. The manner of attachment of the sensor to the pipe can be achieved in a number of ways including the use of epoxy glue, a dry couplant, or compliant material that holds the transducer tightly against the structure to be monitored through the use of a clamp that ensures that the transducer remains snugly fastened on the structure. The sensor can be operated for over 16 hours without a charge and for several days through a solar powered array. The data can be collected and transmitted through a wireless network to the World Wide Web where the data can be stored on a Web Server located on a local computer, transmitted and stored on a remote Web Server hosted by an Internet Service Provider and accessed by another remote computer through a password-protected terminal logged onto the Internet. A transducer can be pulsed or energized by the user and data can be acquired, collected, stored and displayed without the user having direct access to the ultrasonic sensor mounted on the pipe.

FIG. 20 shows an example a graphical user interface located at a user terminal for accessing the transmitting means thereby allowing the user to pulse or energize the transducer in order to transmit the broadband long pulse ultrasonic wave into the mechanical structure to be inspected.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A method for inspecting a wall of a mechanical structure, comprising:
   obtaining an infinite response from a calibration sample having a front face, a thickness, and a back wall, by using one or more transducers for transmitting into the calibration sample an ultrasonic wave having a frequency and duration;
   accessing a user terminal in communication with one or more transducers for transmitting an ultrasonic wave into a mechanical structure to be monitored and for receiving a response signal wave form back from the mechanical structure being monitored;
   transmitting an ultrasonic wave generated by the one or more transducers into the wall of the mechanical structure being monitored at a time (T), wherein the ultrasonic wave has the same frequency and duration as the ultrasonic wave transmitted into the calibration sample;
   receiving a response signal wave form back from the wall of the mechanical structure being inspected; and
   correlating the response signal wave form received back from the wall of the mechanical structure being inspected to the infinite response, thereby creating correlated data from the response signal received back from the wall of the mechanical structure being inspected and the infinite response using a central processing unit in communication with the one or more transducers, wherein said correlated data indicates whether the wall of the mechanical structure being inspected is compromised or damaged.

2. The method of claim 1, further comprising, at a later time (T+1), repeating the steps of (i) transmitting the ultrasonic wave into the wall of the mechanical structure being inspected, (ii) receiving a response signal back from the wall of the mechanical structure being inspected, (iii) correlating the response signal received back from the wall of the mechanical structure being inspected to the infinite response, and further comprising comparing the correlated response signal at time (T+1) to the correlated response signal at said time (T).

3. The method of claim 1, further comprising applying a dry couplant to the mechanical structure between the one or more transducers and the wall to be inspected.

4. The method of claim 1, wherein the one or more transducers are piezocomposite transducers.

5. The method of claim 1, wherein the ultrasonic wave is pulsed for a duration of about 10 μseconds to about 50 μseconds.

6. The method of claim 5, wherein the ultrasonic wave is pulsed for a duration of about 30 μseconds to about 35 μseconds.

7. The method of claim 1, wherein the thickness of the sample material is between about 0.125 inches to about 4.0 inches.

8. The method of claim 1, wherein the one or more transducers used to generate the ultrasonic wave are activated remotely.

9. The method of claim 1, wherein the response signal is received remotely at a server site.

10. The method of claim 9, wherein the response signal is processed remotely at the server site.

11. The method of claim 1, wherein no more than 12 volts of electrical force is required to implement the method.

12. The method of claim 1, wherein the method is intrinsically safe (NRTL).

13. The method of claim 1, wherein the frequency of the ultrasonic wave transmitted into the sample is between about 500 kHz and about 10 mHz.

14. A mechanical structure monitoring system, comprising:
   one or more transducers for transmitting a broadband long pulse ultrasonic wave into a mechanical structure to be monitored and for receiving a response signal wave form back from the mechanical structure, wherein the mechanical structure has a front face, a thickness, and a back wall;
   a central processing unit for eliminating noise from the response signal wave form, said central processor unit in communication with said one or more transducers;
   a means for transmitting the response signal wave form to a remotely-located server and for receiving data back from the remotely-located server; and
   a user terminal for accessing the transmitting means thereby allowing a user to pulse or energize the transducer in order to transmit the broadband long pulse ultrasonic wave into the mechanical structure to be monitored.

15. The system of claim 14, further comprising environmental sensors attached to the mechanical structure to be monitored.

16. The system of claim 15, wherein the environmental sensors can monitor humidity, temperature, moisture, structural vibration, wind, atmospheric volatile organic compounds, or seismic activity.

17. The system of claim 15, further comprising a battery backup for the one or more transducers and environmental sensors.

18. The system of claim 15, further comprising an auxiliary power means for the one or more transducers and environmental sensors.

19. The system of claim 14, wherein the means for transmitting the response signal and for receiving data is a wireless or hard-wired connection to the Internet with secure encrypted data transmission.

20. The system of claim 14, wherein noise is eliminated from the response signal wave form by removing data from the response signal wave form corresponding to the front face of the mechanical structure.

* * * * *